United States Patent [19]

Botstiber et al.

[11] Patent Number: 4,657,671

[45] Date of Patent: Apr. 14, 1987

[54] LIQUID FILTER WITH CHIP DETECTING MEANS

[75] Inventors: Dietrich W. Botstiber, Haverford; David A. Nielsen, Springfield, both of Pa.

[73] Assignee: Aeroquip Corporation, Jackson, Mich.

[21] Appl. No.: 591,040

[22] Filed: Mar. 19, 1984

[51] Int. Cl.⁴ ............................................. B01D 29/38
[52] U.S. Cl. ..................................... 210/86; 210/111; 210/133; 210/168; 210/223; 210/243; 210/304; 210/512.1
[58] Field of Search ................... 210/85, 86, 130, 133, 210/137, 168, 222, 243, 416.5, 420, 443, 446, 450, 456, 223, 111, 304, 512.1

[56] References Cited

U.S. PATENT DOCUMENTS

| | | | |
|---|---|---|---|
| 2,349,992 | 5/1944 | Schrader | 210/85 |
| 2,936,890 | 5/1960 | Botstiber | 210/85 |
| 3,186,549 | 6/1965 | Botstiber | 210/222 |
| 3,317,042 | 5/1967 | Botstiber | 210/86 |
| 3,323,649 | 6/1967 | Rosaen | 210/243 |
| 3,478,494 | 11/1969 | Lustenader et al. | 210/243 |
| 3,870,637 | 3/1975 | Miyoshi et al. | 210/243 |
| 3,878,103 | 4/1975 | Miller et al. | 210/243 |
| 4,053,409 | 10/1977 | Kuhfuss, Jr. | 210/130 |
| 4,205,904 | 6/1980 | Skubich et al. | 210/85 |
| 4,450,075 | 5/1984 | Krow | 210/223 |

Primary Examiner—David Sadowski
Assistant Examiner—Wanda L. Millard
Attorney, Agent, or Firm—Anthony Potts, Jr.; Robert S. Lipton; Robert B. Famiglio

[57] ABSTRACT

A device using intentionally introduced centrifugal force to direct particles suspended in a liquid to peripherally arranged contact members and to detain them there through the static pressure caused by the peripherally moving liquid.

The device separates the ferrous, magnetizable, from the nonferrous, not magnetizable, particles by providing a magnetic capturing unit having a diameter smaller than that of the aforementioned contact member arrangement, so that ferrous particles will be retained by magnetism and so indicated, while nonferrous ones will be detained by the radially more outwardly located contact members and indicated accordingly. Individual indications of, especially nonferrous particle accumulations, are provided for at least two particle magnitude ranges.

11 Claims, 12 Drawing Figures

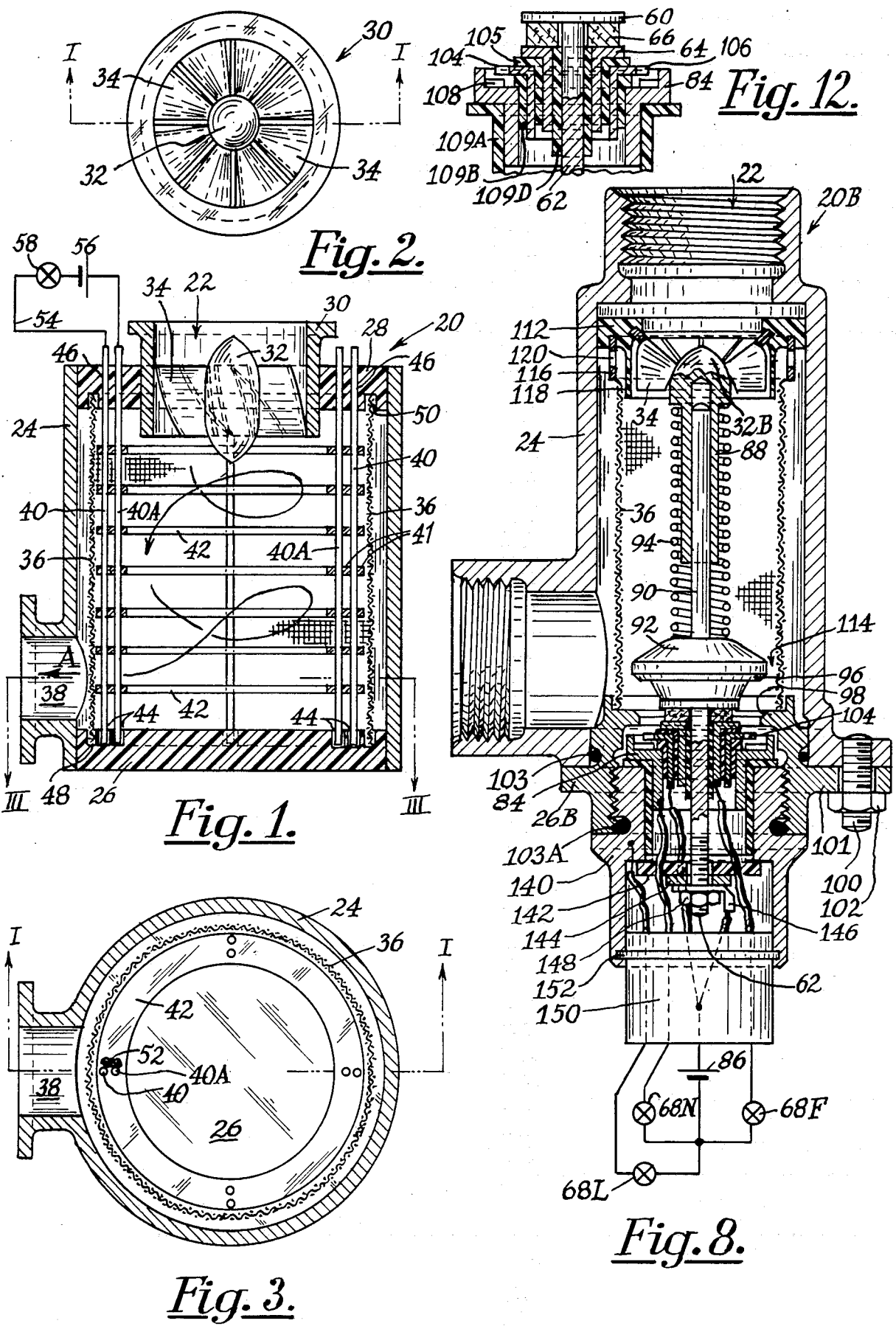

LIQUID FILTER WITH CHIP DETECTING MEANS

BACKGROUND

Various patents of prior art teach methods and devices for the detection of electrically conductive particles suspended in a moving, electrically nonconductive liquid. Especially important is the detection of particles in lubrication systems resulting from the wear and tear of mating mechanical moving parts, such as in internal combustion engines, turbines and comparable ground support and airborne power plants and accessories.

Because particles of the described nature may, firstly, be of either ferrous or nonferrous substances, different methods must be employed to capture all those particles; secondly, considering the possible presence of physically large particles of either composition, a separate and additional detection element appears to be required.

These teachings, which do not cover the entire domain of the particle detection practice, include, but may not be limited to, the following examples and references, presenting at least one typical antecedent for each individual function of possible relevance:

| Bowser | 1,176,732 | March 28, 1916 | (none) |
| --- | --- | --- | --- |
| Matheson | 2,010,435 | Aug. 6, 1935 | (210–43) |
| Lincoln | 2,016,642 | Oct. 8, 1935 | (183–2.7) |
| Schrader | 2,349,992 | May 30, 1944 | (175–183) |
| Scott | 2,375,826 | May 15, 1945 | (92–28) |
| Bourne, Jr. | 2,429,920 | Oct. 28, 1947 | (177–311) |
| Bourne, Jr. | 2,450,630 | Oct. 5, 1948 | (200–52) |
| Vokes | 2,544,244 | March 6, 1951 | (210–166) |
| Botstiber | 2,704,156 | March 15, 1955 | (210–1.5) |
| Botstiber | 2,936,890 | May 17, 1960 | (183–86) |
| Winslow | 2,952,330 | Sept. 13, 1960 | (183–2.5) |
| Botstiber | 2,983,385 | May 9, 1961 | (210–222) |
| Hurby | 3,067,876 | Dec. 11, 1962 | (210–65) |
| Winslow | 3,127,255 | Mar. 31, 1964 | (55–178) |
| Botstiber | 3,317,042 | May 2, 1967 | (210–86) |
| Botstiber | 3,432,750 | Mar. 11, 1969 | (324–41) |
| Kudlaty | 3,628,662 | Dec. 21, 1971 | (210/136) |
| Miller | 3,686,926 | Aug. 29, 1972 | (73/61R) |
| Miller | 3,878,103 | Apr. 15, 1975 | (210/243) |
| Tauber | 4,199,443 | Apr. 22, 1980 | (210/85) |
| Tauber | 4,282,016 | Aug. 4, 1981 | (55/204) |

The foregoing enumeration of prior art indicates that, while specific significant features are present in various teachings, the operationally required wide performance characteristics of the subject invention can not be observed in that prior art.

Reviewing the prior art more selectively, in U.S. Pat. No. 3,317,042 both a method and a device are described for the detection of electrically conductive particles in a moving liquid. In that invention, a screen, or filter is used to guide the particles towards electrical contacts which, when bridged by one or more conductive particles, will close an electric circuit. Other patents, such as U.S. Pat. Nos. 3,686,926 and 3,878,103 use a screen in which the fibers are of conductive materials, alternatingly connected to electrical lines of different polarities and separated from each other by insulating members. All these devices have the deficiency of insufficient contact pressure of the particles on the electrically conductive members of the detecting device; the particles are small and light in weight; buoyancy in the liquid acts to aggravate this condition and as a result, the contact pressure is too low to produce a reliable electric circuit. For ferrous, i.e., magnetizable particles, this deficiency can be alleviated by combining the detector contacts with a magnet, as in U.S. Pat. Nos. 2,936,890 and 3,432,750. Of these, the former applies to ferrous particles only, the latter uses the magnetic effect to attract ferrous particles, while nonferrous particles are still subject to the above-mentioned deficiency in detection. The devices based on alternatingly connected screens do not offer the contact pressure increasing effect of magnetism; they detect ferrous as well as nonferrous particles indiscriminately, with the above-mentioned shortcoming in contact conductive effect. Also, they have the disadvantage of requiring large areas of such alternatingly connected, separately insulated grids or weaves, with the resulting high manufacturing cost, unstable construction and difficulty in identifying and removing particles that have become lodged in the grid, or weave.

Most applications for this type of device relate to fluid systems, such as the lubrication oil circuits of engines and mechanical power transmissions, or the liquid systems of hydraulic power and control units. In these, it is desirable to ignore the very small particles produced by normal wear of moving parts, while capturing and indicating the presence of larger particles which are either of alien nature to the system, or are indicative of incipient gradual deterioration and eventual failure of such moving parts. The screens used in the above-mentioned patents may be selected to pass fine and harmless wear particles, while retaining for indication the larger particles. These, however, will then be subject to the above-mentioned problem of insufficient electrical contact pressure and conductivity.

In U.S. Pat. No. 4,282,016 a device is described, which separates particles and air from a flowing liquid by subjecting both substances to a centrifugal force of rotation of the liquid. In this system, the separating effect for small, normal wear particles is absent. A particle sensor introduced into a device according to that patent will not indicate nonferrous particles, but will have to rely on the magnetic effect for ferrous particles only, such as in U.S. Pat. No. 2,936,890. It would be possible to equip such devices with self-closing particle sensors, such as described in U.S. Pat. Nos. 2,704,156 and 2,983,385. The above-mentioned particle detectors of the screen type, namely, U.S. Pat. Nos. 3,686,926 and 3,878,103, do not offer the advantageous use of such self-closing sensor arrangements, which make them impractical for removal and inspection of captured particles, a feature which is of utmost importance in all systems which do not permit shut-down and drainage of the fluid system during operation.

SUMMARY OF INVENTION

This invention extends to a liquid filter with chip or particle detection means for stationary, mobile and airborne use in crank cases, gear cases, transmissions, oil sumps, tanks, in conjunction with lubrication systems for mechanical equipment which utilize a fluid such as oil.

It is the objective of this invention to effect improved contact pressure for conductive particles on the detector contacts, in order to obtain reliable electrical circuit action for the operation of an indicating system.

It is a further objective of this invention to obtain separate electrical signals for ferrous and for nonferrous particles.

It is another object of this invention to capture excessively large particles and to indicate their presence accordingly and separately.

It is yet a further objective of this invention to make possible a structurally strong and compact construction of the device in its entirety.

It is another objective of this invention to make possible the removal of the captured ferrous and nonferrous particles without spillage or drainage of the fluid system and without interrupting the movement of the liquid.

Still another objective of this invention is to provide additional, desirable features such as the removal of air entrained in the liquid and the prevention of obstruction of flow in case the system becomes excessively saturated with solid particles.

Additional advantages of the subject improvement—per se—and over prior art will become more apparent from the following description and the accompanying drawing.

In the drawing, forming a part of this application:

FIG. 1 is a schematic elevational cross-section in the plane I—I through a liquid filter with chip detecting means having improved contact pressure for electrically conductive particles, FIG. 2 is a top view of the inlet unit of said liquid filter shown in FIG. 1, FIG. 3 is a cross-section of said liquid filter in the plane III—III, FIG. 4 is a schematic cross-section in the plane IV—IV of a liquid filter having separate chip detecting means for ferrous and nonferrous particles, respectively, FIG. 5 is a cross-section in the plane V—V of the liquid filter portraying, especially, the operational vanes, gaps and indicating means, FIG. 6 is a plan view of a possible form of a particle bridge for the detection of nonferrous particles, FIG. 7 is an end view of a particle bridge shwon in FIG. 6, FIG. 8 illustrates, in elevational cross-section a liquid filter having three typical chip detecting means and equipped with a removable particle-carrying member and with a self-closing valve, FIG. 9 portrays in plan view a typical contact configuration for the detection of nonferrous particles, FIG. 10 shows a liquid filter unit with chip detecting means having a circularly-shaped entrance chamber, FIG. 11 is a cross-section in the plane XI—XI of the respective liquid filter unit housing and FIG. 12 is an enlarged, schematic elevational cross-section of only the three typical particle detection components of the filter shown in FIG. 8.

DETAILED DESCRIPTION

Figure 5:
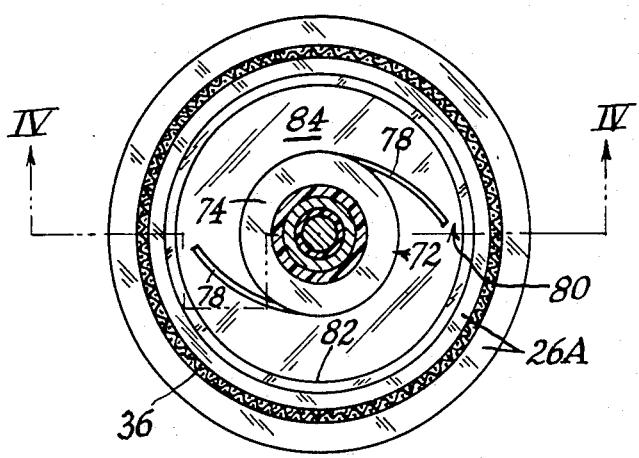

Referring now to the drawing, wherein like reference numerals designate like or corresponding parts, and more particularly to FIGS. 1, 2 and 3, illustrating the method with which the first listed objective of this invention is accomplished, the filter 20 has an upper opening 22 in its substantially cylindrical metal housing 24, which is closed at its lower end by a bottom piece 26 of, in this example, an electrically nonconductive material having various annular grooves formed therein and equipped at its upper end with an annular top member 28 of, in this case, an electrically nonconductive material having various annular grooves and holes formed therein. A cylindrical inlet unit 30 having a cylindrical center piece 32 mounted in its center hole is, in turn, mounted in the center hole of said annular top member 28. The center piece 32 is held in place through a plurality of helically-shaped vanes 34 positioned radially between said inlet unit 30 and said center piece 32, so that the liquid entering at the upper opening 22 and flowing through the housing 24 will be imparted a rotary centrifugally and helically downward motion as indicated by the flow path symbol and arrow "A", tending to drive the liquid towards the cylindrical filter or strainer 36, through which the liquid, together with particles smaller than the strainer openings may pass into the space between strainer 36 and housing 24, the latter extending into an outlet opening 38. In its rotation within the cylindrical strainer 36, the liquid drives solid particles towards that strainer, where they will move in a helical path inside the strainer 36. At one position within that strainer, near its inner circumference, a pair of rods 40 and 40A of electrically conductive material is placed essentially parallel to the strainer axis whereby, for example, the rod 40 is the one radially near the strainer 36 and the rod 40A radially near the rod 40. The distance between the rods 40 and 40A is selected to be of a magnitude to conform to the smallest size of particles to be detected. The rods 40 and 40A are supported and held in place by a number of spacer rings 42, which consist of an electrically nonconductive material, and lodged in the through-holes 41 formed at appropriate locations in said spacer rings 42, in recesses 44 in the bottom piece 26 and through-holes 46 formed in the top member 28. The strainer 36 is arrested in groove 48 of the bottom piece 26 and in the groove 50 of the top member 28. The tangential component of the essentially circular movement of the liquid pushes particles against the rods 40 and 40A, effecting a contact pressure which depends on the aspect area of the particles and the tangential velocity of the liquid. The particles will come to rest on the spacer rings 42 and remain there, being pressed against the conductive rods 40 and 40A. As they bridge the space between the rods, as shown for one particle aggregation 52 in FIG. 3, they close the electric circuit 54 energized by the source 56, causing the indicator lamp 58 to light or to effect another alarm or signal.

In principle, one such pair of rods 40 and 40A would suffice for the basic effect described above, but design considerations may indicate the desirability of more than one set of rods within the circumference of the strainer, or more than two rods in one set; for example, FIG. 3 shows four sets of rods within the circumference.

Another modification and possible simplification is the mounting of only one rod 40 at each position along the stack of spacer rings 42, each such rod being spaced apart radially and inwardly from the strainer 36 for a distance suitable for the capturing of a predetermined minimum particle size; to indicate an accumulation of electrically conductive particles for this arrangement, each single rod 40 has to be connected with one pole of an electric alarm circuit, whereas the strainer 36 will be connected with the other electric pole of the alarm system (not shown), to indicate the collection of particles between a rod 40 and the strainer 36.

The sets of rods 40 and 40A may be electrically connected in parallel, the effect of which will be that one particle bridging one gap of any one rod sets will close the electric signal circuit. This will be the desired function for certain systems, that are considered sensitive to even the smallest amount of metal contamination. However, in some systems, it is desired to get a signal only after more than one particle has been retained. Such an effect can be obtained with great probability by connecting two or more of the rod sets in series. The electric circuit will then be activated only after each of these two or more rod sets have been bridged by particles.

If more than one pair of rods 40, 40A is employed, other than just straight rods parallel with each other and the strainer and in electrical connections varying from those described in the foregoing may be selected, without requiring additional guidelines.

The principle is, in any such arrangement, the use of alternately connected rods, or wires, or conductive, protruding members to obstruct the free movement of particles driven by the rotating motion of the liquid.

Obviously, the foregoing method and equipment does not differentiate between the capturing of ferrous and nonferrous particles.

Figure 4:
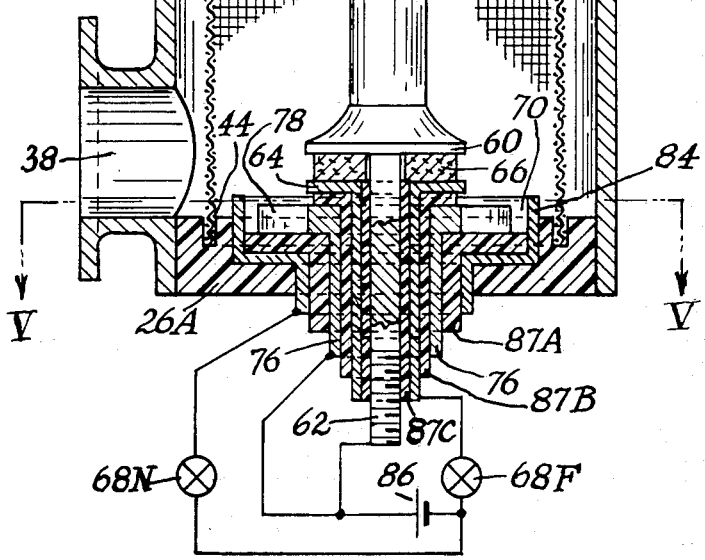

It is sometimes desired and required to indicate the presence of ferrous and nonferrous particles separately. For such a requirement, the principle of this invention may be extended to provide for one sensing arrangement to attract ferrous particles, while nonferrous particles are detected by the above-mentioned circulation of the liquid and its effect of holding particles against a gap formed by two conductors connected to alternate electric polarities. Such an arrangement is shown in FIG. 4. The liquid enters in the same manner as in FIG. 1, through the upper inlet 22 of the filter 20A having a rotation-inducing system of guide vanes 34. The center support 32A is extended downward towards the outlet 38. Near the lower end of the center support 32A, its diameter increases to match the diameter of a first disc 60 of magnetizable material, which extends in its center with a downwardly directed pin 62. The disc 60 abuts with a magnet 66 which, in this case, is shown as an electrically insulating, ceramic, permanent magnet, as used in my U.S. Pat. No. 2,936,890. At a lower surface, a second disc 64 of a magnetizable, ferrous, material is arranged. The magnetic axis of the magnet 66 is oriented axially, i.e., through the thickness of the magnet 66, so that the discs 60 and 64 will form pole pieces of opposite magnetic polarity, producing a magnetic field over the cylindrical surface of the magnet 66. This magnetic field attracts ferrous particles in the liquid, making them adhere to the pole pieces formed by the discs 60 and 64 and close the gap between them, thus activating a signal circuit 68F, indicating the presence of ferrous particles.

The nonferrous particles will remain unaffected by the magnetic field provided by the above-described component parts; they will circulate with the liquid and descend into the cup-shaped cavity 70 below the magnet 66. In this cavity is located a conductive member 72 consisting of a hub 74 with a downward extension 76 and one or more vanes 78, appearing more clearly in FIG. 5. As the particles move in a circular path with the liquid, they tend to move towards the larger radius of the cavity 70, where they will be guided by the vanes 78 towards the inner circumference of the outer cup-shaped part of the cavity 70 to be pushed against the gap 80 between the outer end of a vane 78 and the lateral surface 82 of the essentially, upwardly open, cup-shaped part 84, thus closing an electric circuit consisting of the parts 84, 78, 74 and 76, together with the coacting source of electric voltage 86 and its respective signal 68N.

Both the top member 28A and the bottom member 26A in FIG. 4 are made of an electrically nonconductive material, like the examples for the filter construction in FIG. 1. Insulating members 87A, 87B and 87C are positioned between conductive parts of disassociated electrical polarities.

The previously described effect of obtaining approximate quantitative indication of nonferrous particles by using more than one set of contacts and connecting them in series may be had by making the two basic contacts of the nonferrous indicator, namely, the inner cup surface 82 and the inner member 74, 76 and 78 in several sectors which may be separated by radial gaps in the conductive parts. This provision would not change the basic arrangement shown in FIG. 4, but it is not indicated in the drawing, FIG. 4, in order not to introduce unnecessary intricacies.

It should be noted that all structural parts of the filter 20A are identical with those of the filter 20 shown in FIG. 1. and not necessarily completely repeated in FIG. 4 not to impair the clarity of the significant factors of this illustration.

In the above-described arrangements, particles caught by the electric strainer set, or sets, can be removed and inspected only by disassembling the filter unit, which necessitates stopping the flow of the liquid and draining the system. In another version shown for a chip detecting liquid filter or strainer based on the principles of this invention, this inconvenience can be avoided, the particle carrying member can be removed without draining the liquid from the system and additional advantages may be realized, as shown and described in the following.

Such a device 20B is illustrated, in cross-section, in FIG. 8. The liquid enters at the upper opening 22 of the substantially cylindrical housing 24. Helical vanes 34 impart the rotating motion on the liquid which rotates inside of the cylindrical strainer 36. The essentially cylindrical center support 32B for the vanes 34 further supports a center piece extension 88 in which there is arranged an axially movable rod 90, which extends downward onto a poppet-shaped valve member 92. This poppet 92 is biased against a downward movement by an expansion spring 94, which, in the version shown here, urges against the upper flange surface of the poppet 92. The latter may be shaped to effect an improved downward movement of the rotating liquid. On its largest diameter, the poppet carries a chamfer, or rounded edge 96 which, when downward movement of the poppet is made possible, will seat on a matching ring surface 98 of the bottom piece 26B, which is removable from the strainer housing 24 by conventional fastening means, such as a flange 101 with threaded bolts 100 and binding nuts 102, of which only one each is shown in FIG. 8. A customary "O"-ring 103 is lodged between the bottom piece 26B and the bottom opening of the housing 24.

Figure 9:
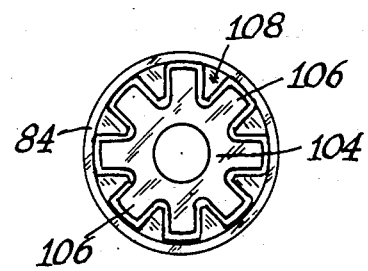

It should be noted that the following details can be observed in both FIG. 8 and in the enlarged particle detecting subassembly in FIG. 12. The lower end surface of the poppet 92 abuts with the top surface of a first disc 60 having a downwardly extending pin 62. The disc 60 is of a magnetizable material such as steel. Underneath the disc 60 is located an annular permanent magnet 66, which, in this example, is shown as an electrically insulating, ceramic magnet as used in my U.S. Pat. No. 2,936,890. At the underside of that magnet 66 is a second disc 64, also of a magnetizable material, forming the counterpart to said first disc 60, so that parts 60 and 64 will act as the two pole pieces of a magnet system consisting of the parts 60,66 and 64. Ferrous particles in the liquid will be attracted to this magnet system and tend to bridge the gap between parts 60 and 64, occupied by the magnet 66. Disregarding possible combinations of parts to simplify the capture of ferrous vs nonferrous parts and the respective indication signals, the following arrangement will be described as a system attaining an optimum differentiation between ferrous and nonferrous particle capture and indication. Under the ferrous second disc 64 is a substantially cylindrical insulating member 105 having the cross-section of an inverted "L". Underneath this insulating member 105 is arranged a conductive, but not magnetizable contact 104 having a star-shaped top surface and a cylindrical center sleeve. Its operation can be seen in FIG. 9. The radial spokes 106 extend from the cylindrical sleeve of part 105 to the cavity of the cup-shaped part 84 at the circular bottom of which spokes 108 are mounted interposed in depth with the spokes 106 of part 104. The axial distance between the radial spokes 106 of part 104 and those of part 108 is smaller than the circumferential distance between the radial spokes 106 of part 104 and those of 108 is smaller than the circumferential distance between the spokes of either one of these, so that particles circling around in the circular cavity 84 will fall through the spokes 106 of part 104 and be caught between the spokes 106 of part 104 and part 108, thus bridging the electrical gap and activating the nonferrous alarm 68N. Particles even larger than the circular distance between the spokes 106 of part 104 will stay on top of these spokes and touch the inner rim of the circular cavity of part 108 and thus bridge the contact gap to also cause the closing of the alarm circuit for the indicator 68N. In this example, the electrically conductive housing 24 is "grounded", requiring the following insulating members placed between the parts 24, 84, 104, 64 and 62 and in the same sequence: 109A, 109B 105 and 109D, readily so identified in FIG. 12.

Figure 6:
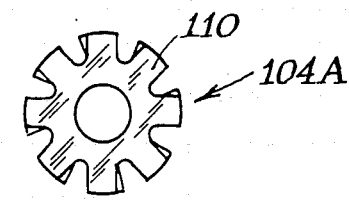
Figure 7:
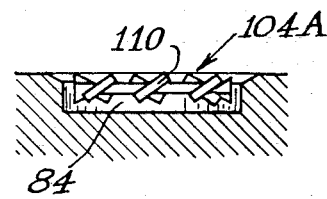

The above-mentioned arrangement of radial extensions for effecting a nonferrous particle bridge may also be accomplished by giving the radial spokes 110 of the nonmagnetizable detector contact 104A an essentially slanted shape, which, due to the basically circular nature of this component will form helical vanes 110, as shown in FIGS. 6 and 7 in axial and radial view, respectively. The spokes or protrusions 108 on the outer part 84 in FIG. 9 may then be omitted as the spaces under the spokes 110 of part 104A will form wedge-shaped openings over the flat bottom of the cavity of part 84. In these wedge-shaped spaces, the particles to be detected will be caught and their rotating movement stopped, while the further rotating liquid will apply pressure to improve the conductive contact.

By making the cylindrical filter support 112 at the top of the screen 36, FIG. 8, which also supports the rotating-inducing guide vanes 34, of an electrically insulating material, the inner section consisting of support 88, spring 94 rod 90 and poppet 92 will be insulated from the screen 36 and the filter housing 24. If the screen is made of a conductive material, such as a perforated or woven metal or wire screen, then the annular radial gap 114 between the poppet 92 and the screen 36 will act as a retaining restriction for particles of larger size than expected to proceed to the particle detecting area below the poppet. By introducing a signal into the circuit formed by the above-mentioned poppet center unit 92 and the screen 36, or any parts electrically connected to it, a signal for large particles will be activated from a common source of electric power 86. This will then act as an indicator 68L of particles of unusually large sizes.

Where large quantities of contamination are expected in the liquid, the filter or strainer may become clogged with solid particles, resulting in reduced open filter area and correspondingly increased pressure drop in the fluid system. The current approach to this effect, which may become critical to the functioning of the equipment served by the fluid system, is to indicate the increased pressure drop by a warning signal, operated by the difference between inlet pressure and outlet pressure. Where interruption of fluid flow can not be tolerated, a check valve under spring pressure may be interposed between inlet and outlet, so that clogging of the filter will cause the liquid to bypass the filter. In the filter arrangement according to this invention, the circular and downward direction of the liquid flow is used to obtain the desired bypass effect upon filter clogging. The filter support 112 is extended into a shroud 118, which is oriented downward in the direction of fluid flow and shields the liquid from flowing to the overflow openings 120 formed in the ring member 116, so that during normal filter operation there will be no flow, or only an insignificant amount of liquid flow through these openings 120. Upon increased pressure difference between inlet and outlet, the liquid will be forced to partly overcome the circular and downwardly directed effect of the guide vane unit 34 as shown in FIGS. 1, 2, 4 and 8 and will reverse its flow direction to upwards and bypass the filter through the overflow openings 120.

Figure 11:
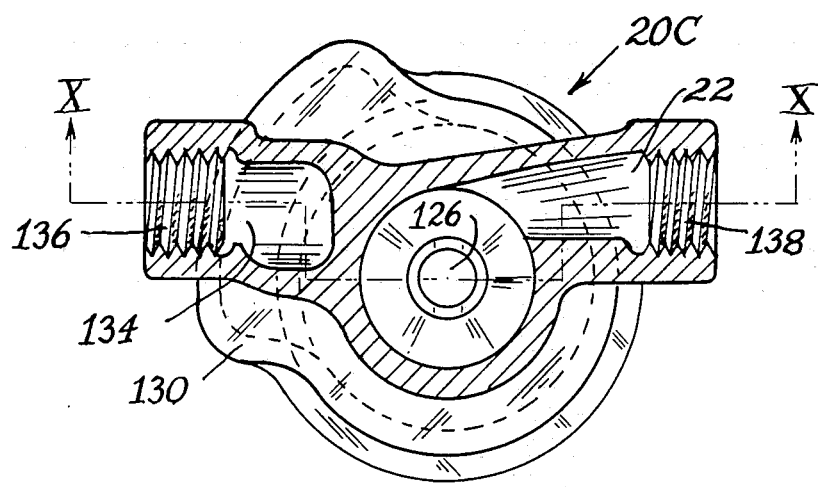
Figure 10:
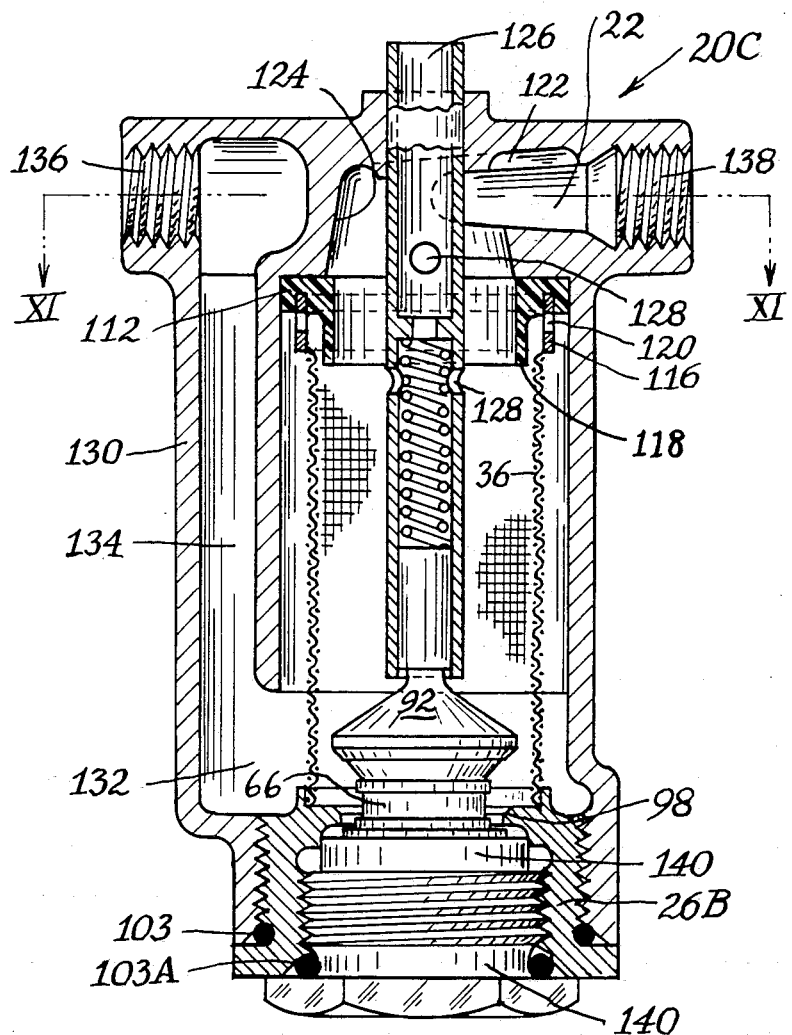

The circular-downward flow of the liquid, which is effected as shown in FIGS. 1, 2, 4 and 8 by a circular arrangement of guide vanes 34, can also be obtained by using a circular shape of the entry chamber 22 in FIGS. 10 and 11. By introducing the liquid at an angle to the axis of the filter at, approximately, 90 degrees and at a slightly downward direction and causing the liquid to be deflected into a circular path, such a circular-downward flow may be obtained. It is enhanced, as shown for filter 200 in FIG. 10, by giving the top chamber an angular top surface 122. A conical shape of the entry chamber, as shown by item 124 in FIG. 10, further directs the liquid flow in the desired circular-downward direction.

The entire interior parts assembly is mounted on the gland 140 for filter 20B, FIG. 8, or on the equivalent member for the filter 20C, FIG. 10. Describing these component parts for only the filter 20B, FIG. 8, an insulating washer 142, a pressure-distributing metal washer 144, a wiring lug 146 and a binding nut 148 applied to the pin 62 constitute this subassembly. A customary "O"-ring 103A is inserted between the bottom piece 26B and said gland 140 for either filter version.

A conventional, in this case, four-pin male receptacle 150 of an electrical connector is mounted by crimping over its edge 152 in said gland 140 so as to accommodate the corresponding female plug of an electrical connector (not shown). Wires leading from the, in this case, grounded gland 140, the cup-shaped part 84, the second disc 64 and the wiring terminal lug 146 of the pin 62, respectively, are connected with a corresponding pin of said four-pin receptacle 150. The external connections and accessories, namely, the voltage source 86 and the signal indicators 86F, 86N and 68L are shown schematically, all in FIG. 8.

To accomplish one of the listed additional objectives, shown of FIG. 10, consists in the specific form given the support for the center member which carries the spring-loaded poppet valve 92, namely, by extending said support upwardly through the housing as a hollow cylinder 126. As the liquid circulates, centrifugal forces impart an accelerating effect, which imposes pressure on entrained air, vapor or gases in the liquid. The effect is that such lighter media are driven toward the center, where they enter the hollow cylindrical center of member 126, from where they may be ducted into a desired location, such as a reservoir of the fluid system, which is usually vented to atmosphere. It should be noted that in this manner the effect endeavored by U.S. Pat. No. 4,282,016 is obtained without the extensive means described in that patent.

By providing the filter housing 130 with a radial bottom opening 132 which connects to an axially-parallel chamber 134, shown in FIGS. 10 and 11, the outgoing flow may then be directed to an outlet port 136, which is in line with the inlet port 138. This in-line arrangement is desirable for purposes of installing the unit in a horizontal duct, thus obviating the changes of direction necessitated by the arrangements described in U.S. Pat. Nos. 4,199,443 and 4,282,016.

It should be noted that various component parts shown and described in the foregoing for filters in accordance with this invention may be substituted for parts made of materials other than originally specified, without departing from the operational intent and the spirit of this concept. More specifically, electrically nonconductive materials may be replaced by electrically conductive ones, provided another insulating member is added at the appropriate position. Comparable situations may exist at the magnetic subassemblies throughout this specification, whereby the herein shown, but illustrative, electrically nonconductive ceramic permanent magnets may readily be substituted through permanent magnets of an electrically conductive material, a substance containing rare earths and through electromagnets, selectively, in combination with insulating members as operationally required.

It is further understood that the herein shown and described embodiments of the subject invention are but illustrative and that variations, modifications and alterations are feasible within the spirit of these teachings.

What is claimed is:

1. A filter for the capturing and indication of, metallic nonferrous, electrically conductive and ferrous, magnetically and electrically conductive respectively particles of varying magnitudes suspended in nonconductive liquids, comprising:

a substantially cylindrical, preferably metal housing having an upper opening, and solid bottom, and an outlet formed therein, a rotation-inducing member having an inlet shape mounted within said upper opening, a cylindrical strainer mounted inside of and near the lateral inside surface of said cylindrical metal housing to strain and confine said electrically conductive particles within the intended rotational liquid travel, at least one pair of rods of an electrically conductive material positioned axially, but radially with respect to each other, concentric with and near the inside perimeter of said strainer so that the gap aspect area between said rods is radially with respect to the tangential liquid flow, said at least one pair of rods of an electrically conductive material consisting of a pair of electric contacts connected with a signal circuit, a plurality of spacer rings, having holes formed therein, of an electrically nonconductive material arranged axially and spaced apart from each other axially within said filter housing and inside of said cylindrical strainer so as to secure said pairs of electrically conductive rods, within said holes formed in said spacer rings and to provide horizontal areas for the capturing and the collection of said conductive particles, to expose them to the static pressure exerted by the passing liquid, to establish a dependable electric contact among each said rod pair to result in the closing of an electric circuit and a reliable signal and alarm, respectively.

2. A filter as defined in claim 1, wherein, said cylindrical strainer is of an electrically conductive material and electrically insulated from said cylindrical housing, made of metal, said cylindrical strainer adapted for the connection with one pole of an electric signal and alarm circuit, selectively, at least one rod of an electrically conductive material arranged axially distant from the inside perimeter of said electrically conductive strainer, said at least one rod adapted for the connection to another pole of an electric signal and alarm circuit, selectively, thus providing areas for the capturing and the collection of said conductive particles between each said single rod and said electrically conductive strainer, thereby establishing a dependable electric contact resulting in a reliable signal and alarm, respectively.

3. A filter as defined in claim 2, wherein, the electrical connections of the rod-to-rod and the rod-to-strainer configuration, respectively, are in parallel to allow for a signal or alarm upon the presence of electrically conductive particles across a single said rod configuration.

4. A filter as defined in claim 2, wherein the electrical connections of the rod-to-rod and the rod-to-strainer configurations, respectively, are in series so that each contact set of this configuration must be bridged by electrically conductive particles to complete the entire signal or alarm circuit.

5. A filter for electrically nonconductive liquids containing metallic, partly nonferrous, electrically conductive and partly also ferrous, magnetically and electrically conductive particles suspended therein, having inlet and outlet flanges for its connection with incoming and outgoing hydraulic line, respectively, comprising in combination;

a means for imparting a centrifugally rotating downwardly helical motion on the liquid together with the therein suspended metallic particles when entering the filter through the inlet of said filter;

a means for the capturing of solely magnetically conductive, ferrous, metallic particles positions, remotely from the general path of the circulating liquid, at the axis of rotation of the liquid and apart from the means for capturing of nonferrous particles, and wherein electric contacts are provided at or near said means for the capturing of solely ferrous particles for the connection with an electric circuit adapted to indicate the presence of collected ferrous particles separate from any nonferrous particle collections and signals;

a means for capturing nonferrous particles of a first magnitude range;

a means for capturing nonferrous and other particles of a second magnitude range larger than said first magnitude range;

a means for the indication of said captured particles jointly and for individual particle quantities, varieties, and magnitude ranges, selectively; and a means for the liquid to bypass the filter when clogged.

6. A filter for electrically nonconductive liquids containing metallic, partly nonferrous, electrically conductive and partly also ferrous, magnetically and electrically conductive paticles suspended therein, having inlet and outlet flanges for its connection with an incoming and an outgoing hydraulic line, respectively, comprising in combination:

a means for imparting a centrifugally rotating downward helical motion on the liquid together with the therein suspended metallic particles when entering the filter through the inlet of said filter;

a means for capturing solely ferrous particles;

a means for the capturing of, primarily, nonferrous, metallic, electrically conductive and nonmagnetizable particles comprising an upwardly-open, cup-shaped part having a diameter exceeding that of the ferrous particle capturing means and connected with one pole of an electric power source, and a hub positioned in the center of said cup-shaped part but electrically insulated from it and connected with the other power source pole, and at least one curved vane extending substantially radially from said hub toward the lateral inside surface of said cup-shaped member leaving a gap allowing for the passing of the liquid but adapted to arrest said, primarily nonferrous particles, per se, and separate them from any other particle collection, resulting in the closing of a signal circuit indicating said nonferrous particle presence;

a means for the indication of said captured particles jointly and for individual particle quantities, varieties, and magnitude ranges, selectively; and a means for the liquid to bypass the filter when clogged.

7. A filter for electrically nonconductive liquids containing metallic, partly nonferrous, electrically conductive and partly also ferrous, magnetically and electrically conductive particles suspended therein, having inlet and outlet flanges for its connection with an incoming and outgoing hydraulic line, respectively, comprising in combination:

a means for imparting a centrifugally rotating downwardly helical motion on the liquid together with the therein suspended metallic particles when entering the filter through the inlet of said filter;

a means for capturing solely ferrous particles;

a means for the capturing and retaining of, primarily, nonferrous, nonmagnetizable particles comprising: a stationary inner nonmagnetizable, electrically conductive contact member of a substantially star-shaped configuration, having a plurality of radial spokes of truncated-helical form, connected to one pole of an electric signal circuit, and an outer nonmagnetizable, metallic, electrically conductive contact member having the shape of a substantially cylindrical upwardly-open cup the flat bottom of which is for a small gap distance below the lowest edges of said truncated-helical blades, connected with another pole of said electric signal circuit, said inner contact member positioned within and electrically insulated and spaced by said small gap distance from said outer contact member, said helically formed blades adapted to direct said particles toward the outer and lower contact member so as, upon becoming captured in said small gap, to complete said electric circuit between said inner and said outer contact member indicating a signal or alarm, respectively;

a means for the indication of said captured particles jointly and for individual particle quantities, varieties, and magnitude ranges, selectively; and a means for the liquid to bypass the filter when clogged.

8. A filter for electrically nonconductive liquids containing metallic, partly nonferrous, electrically conductive and partly also ferrous, magnetically and electrically conductive particles suspended therein, having inlet and outlet flanges for its connection with an incoming and an outgoing hydraulic line, respectively, comprising in combination:

a means for imparting a centrifugally rotating downwardly helical motion on the liquid together with the therein suspended metallic particles when entering the filter through the inlet of said filter;

a means for capturing of solely magnetically conductive, ferrous, metallic particles are positioned, remotely from the general path of the circulating liquid, at the axis of rotation of the liquid and apart from the means for the capturing of nonferrous particles;

a means for capturing nonferrous particles of a first magnitude range;

a means for capturing nonferrous and other particles of a second magnitude range larger than said first magnitude range;

a means for the indication of said captured particles jointly and for individual particle quantities, varieties, and magnitude ranges, selectively;

a means for the liquid to bypass the filter when clogged; and a means for the automatic closing of the bottom of a filter housing upon the removal of the particle-detecting units is provided to prevent drainage of the working fluid and to allow for inspection, maintenance or replacement of the particle capturing means, and said means comprising a spring-biased poppet adapted to seat on a circular surface of a round opening in the removable bottom piece upon the removal of said bottom piece together with the therein mounted particle capture and detention units.

9. A filter as defined in claim 8 wherein said poppet together with its assembly and operational component parts is electrically insulated from said filter housing and its filter, the diameter of said poppet being smaller for a predetermined dimension than the inside diameter of said filter, thereby establishing an annular gap between said component parts, and said poppet and said filter being connected with the respective poles of an electric signal or alarm circuit to indicate the presence of particles of a second, larger, magnitude range captured in said gap.

10. A filter as defined in claim 8 wherein, a hollow, tubular extension is provided as the center support of said spring-biased poppet, said center support extending through and beyond the top of an inlet chamber, and said hollow, tubular extension having radial openings formed therein to permit air, or gas, or vapor collecting at the center of the rotating liquid to exit upwardly and against the flow direction of the liquid.

11. A filter for electrically nonconductive liquids containing metallic, partly nonferrous, electrically conductive and partly also ferrous, magnetically and electrically conductive particles suspended therein, having inlet and outlet flanges for its connection with an incoming and outgoing hydraulic line, respectively, comprising in combination:

a means for imparting a centrifugally rotating downwardly helical motion on the liquid together with the therein suspended metallic particles when entering the filter through the inlet of said filter;

a means for capturing solely ferrous particles;

a means for capturing nonferrous particles of a first magnitude range;

a means for capturing nonferrous and other particles of a second magnitude range larger than said first magnitude range;

a means for the indication of said captured particles jointly and for individual particle quantities, varieties, and magnitude ranges, selectively; and a means for bypassing of the liquid in case of clogging a filter medium comprising:

a first axially short cylindrical frame of essentially the same diameter as that of said filter medium, arranged near the inlet zone of said filter medium and having openings formed therein permitting free passage of the liquid, and a second cylindrical frame of a smaller diameter but longer axial size than and located concentrically inside of said first cylindrical frame, so as to impede the liquid from passing through said openings, so long as the circular and helical flow of the liquid is not obstructed by the clogging of the filter medium.

* * * * *